United States Patent [19]

Brown

[11] Patent Number: 4,675,015

[45] Date of Patent: Jun. 23, 1987

[54] DIAPER WITH SEPARABLE PANEL FOR UMBILICAL CORD

[76] Inventor: Alice Brown, Horizon Hills Apts. #2K, Fortune Rd. W., Middleton, N.Y. 10940

[21] Appl. No.: 834,565

[22] Filed: Feb. 28, 1986

[51] Int. Cl.[4] .............................................. A61F 13/16
[52] U.S. Cl. ................................................ 604/385 R
[58] Field of Search .................... 604/385.1, 394, 395, 604/396

[56] References Cited

U.S. PATENT DOCUMENTS 2,141,105 12/1938 Eller et al. ......................... 604/394

Primary Examiner—John D. Yasko
Attorney, Agent, or Firm—Leighton K. Chong

[57] ABSTRACT

A disposable diaper has a separable panel formed in its front portion over the umbilical area of an infant. The panel has at least one separation line for opening the panel to expose the umbilical cord of a newborn infant and allow it to project therethrough. When the umbilical cord has been eliminated, the panel can be left intact to allow full use of the diaper.

3 Claims, 3 Drawing Figures

DIAPER WITH SEPARABLE PANEL FOR UMBILICAL CORD

This invention relates to diapers and particularly to disposable diapers for newborn infants.

BACKGROUND OF THE INVENTION

Conventional disposable diapers typically have front and back panels which are fastened together around the waist of the newborn infant. However, the still attached umbilical cord of the newborn infant is vulnerable to infection and to frictional irritation by the overlying diaper. The rubbing of the diaper on the umbilical cord when it is still raw can cause inflammation and painful soreness to the infant. The diaper may also trap bacteria at the umbilical site and bring about an infection, particularly when it becomes contaminated with infant feces and urine.

SUMMARY OF THE INVENTION

To solve the problems of conventional disposable diapers, the present invention provides a disposable diaper which has a separable panel formed in the front portion of the diaper in the umbilical area. The umbilical panel is preferrable in the form of a perforated section which can be separated to allow the umbilical cord of newborn infants to project therethrough, and which later can be left intact when the umbilical cord has been eliminated. The perforated section can be in the form of intersecting lines, and the side portions along the lines can be thermally sealed together to maintain the integrity of the diaper when the umbilical panel is used.

The further details, advantages and other features of the invention are described in detail below in conjunction with the following drawings.

DETAILED DESCRIPTION OF THE INVENTION

The following description describes one of the preferred forms of the invention but is not intended to limit the scope of the invention.

Figure 1:
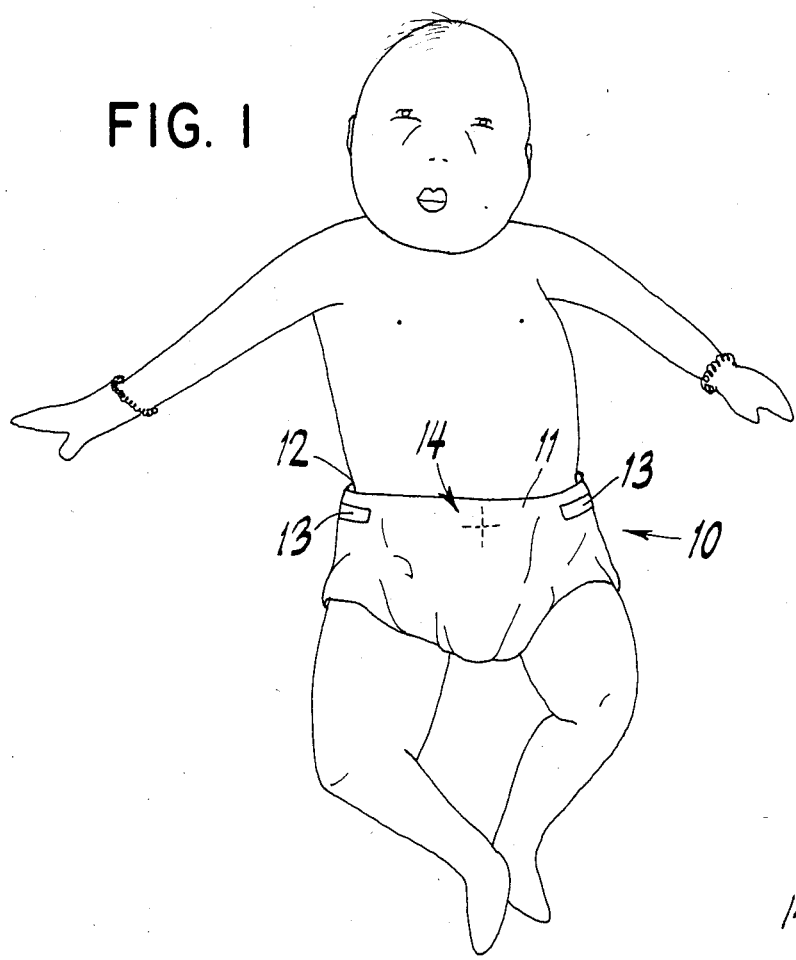
FIG. 1 is a perspective view of the disposable diaper as used on an infant in accordance with the invention.

Referring to FIG. 1, a disposable diaper 10 is formed by a front absorbent portion 11 which continues through a crotch portion to a back absorbent portion 12. The diaper placed around the bottom of an infant and the front and back portions are fastened by adhesive tabs 13 on either side of the infant's waist, as it is used conventionally. An umbilical panel 14 is formed in the front portion 11 in the umbilical area of the infant. In accordance with the invention, the panel is separable into sections to expose an to allow the umbilical cord to project therethrough.

Figure 2:
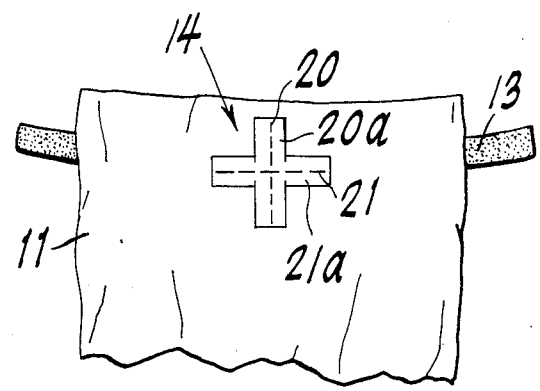
FIG. 2 is a front view of the preferred form of the diaper with an umbilical panel of the invention.
Figure 3:
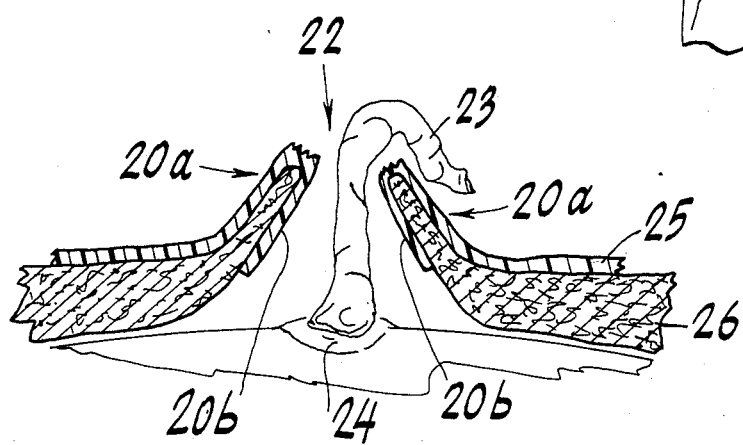
FIG. 3 is a sectional view of the umbilical panel of FIG. 2.

Shown in greater detail in FIG. 2, the preferred form of umbilical panel has two intersecting linear perforations 20 and 21 in the form of a cross, each of which is formed within strip areas 20a and 21a, respectively. FIG. 3 shows one of the strip areas as it appears in use when the perforations 20 and 21 are separated to create an opening 22 through which the umbilical cord 23 is exposed and allowed to extend to the outside air. The opening 22 creates a space between the separated areas 20a of the diaper and the umbilical cord 23 and navel area 24 of the infant, which eliminates frictional rubbing of the diaper on the umbilical area. Outside air circulating in the umbilical area cools the skin and dries the umbilical cord, thereby reducing the possibility of inflammation or infection.

The perforations 20 and 21 and strip areas 20a and 21a are preferrably formed by heat stamping or other methods of thermal forming. The absorbent portion 11 has a plastic outer layer 25 and an inner absorbent layer 26 made of cotton or other absorbent fiber. In the preferred method of manufacture, a plastic tape 20b corresponding to the strip area 20a of the plastic layer 25 is placed on the inside surface of the inner layer 26 in registration with the strip area 20a. The strip area and tape are then heat pressed from above and below at the same time that a cutter cuts a perforation line 20 in the center of the strip area.

The heat pressing deforms and compresses the absorbent layer 26 to provide greater rigidity to the strip area. The perforation produces alternate cuts and areas where the plastic layer and underlying tape are still joined across the perforation line to keep the strip area intact until it is separated by the user to expose the umbilical cord. At the same time, the heat during the thermal forming process joins the thermoplastic material of the external strip area and inside tape such that a seal is formed to keep the ends along the perforation line intact even when the strip area is separated.

Other forms of separable umbilical panel and methods of forming a seal may of course be used. For example, the umbilical panel may be formed as a tear-out square or circle by perforation or forming a weakened tear line, or may be provided as a flap which is bent back to expose the umbilical cord.

The invention has the advantage that when the umbilical cord of the infant has dried and been eliminated, the umbilical panel can be left intact so that the full utility of the disposable diaper can be obtained.

The above described embodiments and all other obvious modifications are intended to be encompassed within the scope of the invention, as defined in the following claims.

I claim:

1. In a diaper having a front absorbent portion provided with a layer of absorbent material which is joined to a back absorbent portion by fastening means at the waistline of an infant, the improvement comprising a panel formed in said front absorbent portion over the umbilical area of the infant, said panel having at least one separation line formed through said absorbent layer of said front absorbent portion, said separation line including means which is manually separable so as to form an opening in said umbilical area extending through said absorbent layer of said front absorbent portion, whereby the umbilical cord of a newborn infant can be exposed and allowed to project therethrough, and said separation line being left intact when it is desired not to expose the umbilical cord and to retain the full absorbing capacity of said front absorbent portion.

2. In a diaper having a front absorbent portion which is joined to a back absorbent portion by fastening means at the waistline of an infant, the improvement comprising a panel formed in said front absorbent portion over the umbilical area of the infant, said panel having at least one separation line for separating at least a portion of said panel so as to form an opening in said front absorbent portion, wherein said panel is formed by two intersecting perforated lines in the form of a cross over the umbilical area, whereby the umbilical cord of a newborn infant can be exposed and allowed to project therethrough.

3. A diaper according to claim 2, wherein said diaper is of the type having a plastic outer layer and an inner absorbent layer, and said panel is formed by two strip areas each having a respective one of said perforated lines in the center thereof, and by two corresponding tape sections of plastic material on an inside surface of said inner absorbent layer each in registration with a respective one of said strip areas, said strip areas, tape sections, and absorbent layer therebetween being heat formed together and perforated to form said panel.

* * * * *